United States Patent
You et al.

(10) Patent No.: US 10,189,790 B1
(45) Date of Patent: Jan. 29, 2019

(54) IMIDAZOLINE COMPOUND, MOBILITY CONTROL SYSTEM, PLUGGING AGENT FOR GAS CHANNELING, AND METHOD FOR CARBON DIOXIDE FLOODING

(71) Applicants: China University of Geosciences (Beijing), Beijing (CN); China University of Petroleum(East China), Qingdao, Shandong (CN)

(72) Inventors: Qing You, Beijing (CN); Caili Dai, Qingdao (CN); Yan Zhang, Beijing (CN); Yifei Liu, Qingdao (CN); Jichao Fang, Qingdao (CN); Huan Wang, Beijing (CN)

(73) Assignees: China University of Geosciences (Beijing), Beijing (CN); China University of Petroleum(East China), Qingdao (CN)

( * ) Notice: Subject to any disclaimer, the term of this patent is extended or adjusted under 35 U.S.C. 154(b) by 0 days.

(21) Appl. No.: 16/029,516

(22) Filed: Jul. 6, 2018

Related U.S. Application Data

(62) Division of application No. 15/716,207, filed on Sep. 26, 2017, now Pat. No. 10,081,604.

(30) Foreign Application Priority Data

Jul. 12, 2017 (CN) .......................... 2017 1 0566128

(51) Int. Cl.
| | | |
|---|---|---|
| *C09K 8/42* | (2006.01) | |
| *E21B 33/13* | (2006.01) | |
| *C07D 233/14* | (2006.01) | |
| *C09K 8/594* | (2006.01) | |
| *C07D 233/20* | (2006.01) | |
| *G01R 33/46* | (2006.01) | |
| *G01N 21/35* | (2014.01) | |
| *E21B 43/16* | (2006.01) | |

(52) U.S. Cl.
CPC ......... *C07D 233/14* (2013.01); *C07D 233/20* (2013.01); *C09K 8/594* (2013.01); *E21B 43/164* (2013.01); *G01N 2021/3595* (2013.01); *G01R 33/46* (2013.01)

(58) Field of Classification Search
CPC ......... C04B 28/02; C04B 14/06; E21B 33/13; E21B 33/14; E21B 47/1015; E21B 43/26; E21B 43/267; C09K 8/44; C09K 8/467; C09K 8/50
See application file for complete search history.

(56) References Cited

U.S. PATENT DOCUMENTS 3,663,351 A * 5/1972 Murphy .................. C08K 3/36
442/394

FOREIGN PATENT DOCUMENTS

CN 104212427 A * 12/2014

* cited by examiner

*Primary Examiner* — Zakiya W Bates
(74) *Attorney, Agent, or Firm* — Calfee, Halter & Griswold LLP

(57) ABSTRACT

An imidazoline compound, a mobility control system, a plugging agent for gas channeling, and a method for carbon dioxide flooding. The structure of the imidazoline compound is represented by formula (1), in which R is pentadecyl, heptadecenyl, or heptadecyl. A mobility control system that contains the imidazoline compound can interact with carbon dioxide to form a plugging agent for gas channeling, and thereby attains a plugging effect for carbon dioxide channeling in a carbon dioxide flooding process.

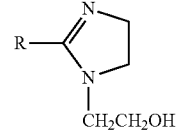

formula (1)

6 Claims, 2 Drawing Sheets

IMIDAZOLINE COMPOUND, MOBILITY CONTROL SYSTEM, PLUGGING AGENT FOR GAS CHANNELING, AND METHOD FOR CARBON DIOXIDE FLOODING

CROSS REFERENCE TO RELATED APPLICATIONS

This application is a divisional of U.S. application Ser. No. 15/716,207, filed on Sep. 26, 2017, entitled "Imidazoline Compound, Mobility Control System, Plugging Agent For Gas Channeling, And Method For Carbon Dioxide Flooding", and claims priority to Chinese Application No. 201710566128.8, filed on Jul. 12, 2017, entitled "Mobility Control System for Carbon Dioxide Flooding in Low permeability or Ultra-low Permeability Oil Reservoirs and Use Thereof", which are specifically and entirely incorporated by reference.

FIELD OF THE INVENTION

The present invention relates to the field of oil recovery efficiency improvement, in particular to an imidazoline compound, a mobility control system that contains the imidazoline compound, a plugging agent for gas channeling formed by the mobility control system, and a method for carbon dioxide flooding utilizing the mobility control system.

BACKGROUND OF THE INVENTION

As a highly efficient energy resource, petroleum plays an irreplaceable role in the national economy. As the national economy in China grows rapidly, the demand for petroleum is increasing continuously. In year 2015, the domestic yield of crude oil was 213 million tons, and the quantity of imported crude oil was 334 million tons, and the foreign-trade dependency was as high as 62%. Hence, efficient exploitation of petroleum is a major demand and important safeguard for national energy security.

As oil and gas exploration and development is deepened, the percentage of exploration and development of low-permeability oil and gas resources has become higher and higher. The average exploration and development percentage of low-permeability oil and gas resources has accounted for about 67% of newly increased proven reserves during the $12^{th}$ 5-year plan; especially in recent years, new proven ultra-low permeability oil reservoirs were especially abundant. In China, ultra-low permeability oil and gas resources have been regarded as a major domain of national oil and gas development.

The oil recovery of ultra-low permeability oil reservoirs recovered by means of natural energy is usually lower than 10%. To improve the oil recovery of those oil reservoirs, the oil reservoir energy has to be supplemented by water or gas injection. However, in a water injection process, a hydrated film may be formed easily, and the clay minerals in the formation swell and the pores tend to be closed when the clay minerals encounter water, resulting in rapidly increased injection pressure and severely decreased injection volume or even failure of injection; consequently, the recovery efficiency of the matrix is very low. Compared with water injection, injected gas is easier to permeate into micro-nano pores, and can effectively displace the crude oil in the matrix; therefore, the oil displacement efficiency can be remarkably improved. Especially, carbon dioxide is usually more dissoluble in water than hydrocarbon gasses, and has higher dissolvability in crude oil than in water. Carbon dioxide dissolved in a water solution can transfer to dissolve in crude oil, and has advantages including high mobility, viscosity reduction, volumetric expansion, interfacial tension reduction, plugging removal by acidization, light hydrocarbon extraction, and easy phase-mixing features, etc. Therefore, carbon dioxide flooding has received extensive concern as an effective method for enhancing oil recovery for low-permeability oil reservoirs in China and foreign countries, and has achieved favorable effects in applications in oil fields. However, oil reservoirs with ultra-low permeability are usually accompanied with natural and/or artificial fractures. As a result, after carbon dioxide is injected into the formation, since the viscosity of carbon dioxide is much lower than that of water, gas channeling may occur easily along the fractures; therefore, the swept volume of carbon dioxide and the oil displacement efficiency are severely decreased, so that the field experiment result is severely degraded. In recent years, domestic and foreign researchers have put forward 5 types of mobility control systems that can be used in the carbon dioxide flooding process and associated methods:

Water Alternating Gas (WAG)

The Water Alternating Gas (WAG) method is the most widely applied and most successful carbon dioxide mobility control method. WAG is to inject water slugs and gas slugs alternatively to the oil reservoir, wherein, water firstly enters into the fractures and form a shield; since a phase interface exists between water and gas, the water saturation is increased, while the gas saturation is decreased, and thereby the relative permeability of carbon dioxide is decreased, the gas transfers into the matrix, the gas-to-oil mobility ratio is improved, the swept volume of gas is expanded, and the purpose of improving oil recovery is attained. However, for oil reservoirs with ultra-low permeability, the follow-up injection is very difficult, and the introduced water will hamper carbon dioxide from mixing with hydrocarbon compounds.

Foam

A foamed system has a "selective plugging" characteristic. The foams can effectively decrease the relative permeability of gas in the porous media, and thereby can effectively control gas mobility in the carbon dioxide injection process; in addition, foam flooding applied in oil fields is relatively successful. The foam flooding effect generated by injecting a surfactant and a gas simultaneously is more advantageous than that generated by injecting the surfactant and the gas alternatively; in addition, by comparing the effect of foam flooding in improvement of vertical sweep efficiency with the effect of polymer flooding, it is concluded that the effect of foam flooding for high-permeability zones is superior to that of polymer flooding. To improve stability of foams, polymer enhanced foam, gelled foam, and three-phase foam are developed. However, foaming agents employed by conventional foam flooding are usually water-dissoluble surfactants. When such a surfactant is used for ultra-low permeability oil reservoirs, the solution of water-dissoluble foaming agent is difficult to inject, and consequently it is difficult to use the foam fluid to control carbon dioxide mobility.

Polymer Viscosifiers

Polymers can be directly dissolved as chemical additives in supercritical carbon dioxide to attain an effect of increasing the viscosity of the supercritical carbon dioxide. Domestic and foreign researchers have studied the influences of supercritical carbon dioxide fluid admixed with polymer viscosifiers on mobility control and sweep efficiency through laboratory experiments and field experiments. Heller et al. has found that polymers can be much more dissolved as mobility control agents in supercritical carbon dioxide, and the structure of polymer, chemical properties of crystal, and molecular weight, etc. have significant influence on the solubility of polymers in carbon dioxide. At present, polymers that have been studied extensively include fluoropolymers and ordinary polymers. Wherein, ordinary polymers are hydrophobic and usually have a problem of poor solubility, which results in a poor viscosifying effect; fluoropolymers have much better dissolvability in supercritical carbon dioxide, and can attain a fairly good viscosifying effect; however, such polymers have their obvious shortcomings: firstly, the production cost is too high to mass production; secondly, the environmental hazard is severe, and adverse to environmental protection.

Gel

The channel plugging mechanism of gel is to utilize a gel solutions to form gel for plugging in the fractured matrix or channels. With reference to gel materials for conformance control, a gel system (e.g., sodium silicate gel) that matches the oil reservoir can be developed according to the actual oil reservoir conditions; specifically, water glass gel generated through a reaction between sodium silicate solution and carbon dioxide is utilized to inhibit carbon dioxide channeling and attain the purpose of achieving mobility control in carbon dioxide flooding. The viscosity of the system is low and equivalent to the viscosity of water; hence, the system has a characteristic of high plugging strength; however, a certain degree of contamination to the matrix of the ultra-low permeability oil reservoir will be resulted.

Precipitation

The basic plugging principle of the precipitation method is to control a salt solution (e.g., magnesium salt, calcium salt, or barium salt) hydrolyzed to an alkaline state or an organic amine (ethylene diamine) to react with injected carbon dioxide to generate carbonate precipitation, and thereby attain an plugging effect. The chemical precipitation method can effectively improve the mobility of carbon dioxide, and can improve the sweep efficiency by about 20-30%. However, it is necessary to note that the pH value of the solution in the actual oil reservoir or the reaction of NaOH with rocks in the oil reservoir will make it difficult to control the pH reasonably during the construction process. Ethylene diamine belongs to small molecular organic amine, and is inflammable, toxic, and harmful to health and environment in itself; in addition, if the oil saturation is high, the plugging strength of the generated precipitate will be decreased.

Though the above-mentioned methods have certain carbon dioxide mobility control capability, they have drawbacks such as unsatisfactory effect, complex operation, environmental pollution, and formation damage, etc.

SUMMARY OF THE INVENTION

To overcome the above-mentioned drawbacks of mobility control systems for carbon dioxide flooding in the prior art, the present invention provides an imidazoline compound, a mobility control system, a plugging agent for gas channeling, and a method for carbon dioxide flooding.

To attain the object described above, in a first embodiment, the present invention provides an imidazoline compound, of which the structure is represented by formula (1):

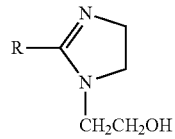

formula (1)

wherein, R is pentadecyl, heptadecenyl or heptadecyl.

In a second embodiment, the present invention provides a mobility control system, which comprises the imidazoline compound in the present invention, a mobility control additive, and water.

In a third embodiment, the present invention provides a plugging agent for gas channeling, which is a mixture obtained by introducing carbon dioxide into the mobility control system in the present invention for gel forming.

In a fourth embodiment, the present invention provides a method for carbon dioxide flooding, which comprises: injecting the mobility control system in the present invention into an oil reservoir, and then injecting carbon dioxide into the oil reservoir for over-displacement; after the mobility control system forms a plugging agent for gas channeling, further injecting carbon dioxide into the oil reservoir for oil displacement.

The present invention has the following beneficial effects:

(1) The mobility control system in the present invention is an intelligent carbon dioxide-sensitive material, which forms a plugging agent for gas channeling and attains a plugging effect for gas channeling after it contacts with carbon dioxide under formation temperature.

(2) The mobility control system in the present invention is applicable to deep plugging for gas channeling in carbon dioxide flooding oil reservoir under 40-90° C. and can increase the swept volume of carbon dioxide flooding; the plugging agent for gas channeling formed by the mobility control system and carbon dioxide has viscosity as high as $1 \times 10^4$-$20 \times 10^4$ mPa·s.

(3) The components of the mobility control system in the present invention are all environment-friendly, don't contain any toxic chemical component, and are favorable for environmental protection and operator's health.

(4) The mobility control system in the present invention has low initial viscosity (only as low as 5-10 mPa·s). It has good injection performance, and can deeply enter into gas channel easily, and thereby achieves deep plugging for gas channeling. It reduces harms to non-target zones. The mobility control system is not only convenient to use in field operation, but also can greatly enhance the oil recovery of the subsequent carbon dioxide flooding.

DETAILED DESCRIPTION OF THE EMBODIMENTS

Figure 1:
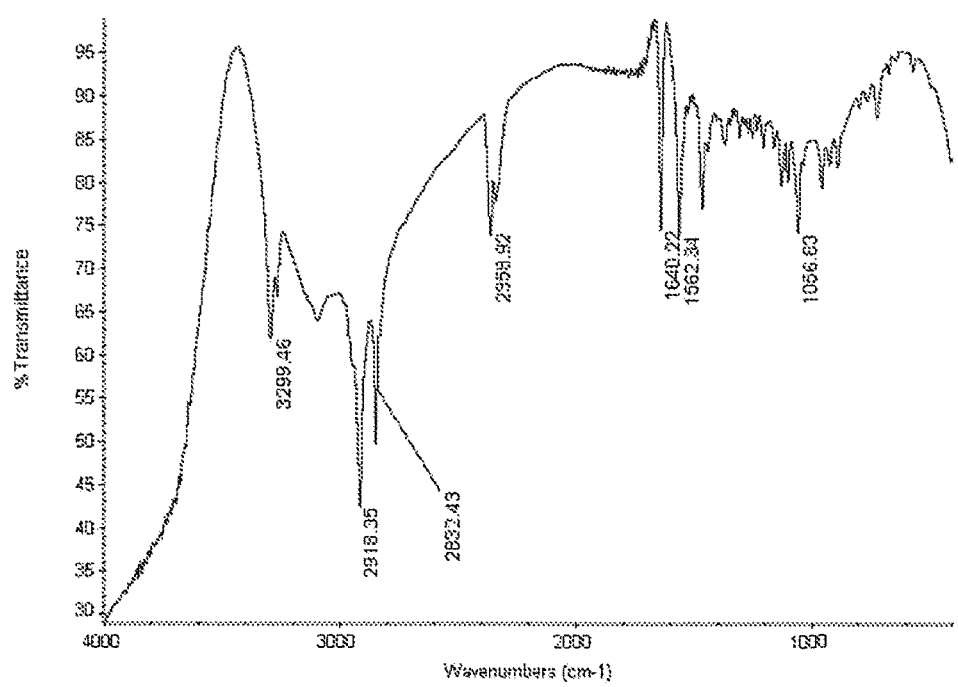
FIG. 1 is an infrared spectrogram of 1-ethoxyl-2-pentadecyl-imidazoline in preparation example 1.

The endpoints and any value in the ranges disclosed in the present invention are not limited to the exact ranges or values; instead, those ranges or values shall be comprehended as encompassing values that are close to those ranges or values. For numeric ranges, the endpoints of the ranges, the endpoints of the ranges and the discrete point values, and the discrete point values may be combined to obtain one or more new numeric ranges, which shall be deemed as having been disclosed specifically in this document.

In the first aspect, the present invention provides an imidazoline compound, of which the structure is represented by formula (1):

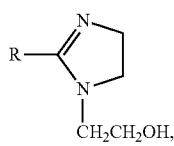

formula (1)

wherein, R is pentadecyl, heptadecenyl or heptadecyl.

In the present invention, the imidazoline compound may be prepared with the following method:

(1) R1-COOH and N-(2-ethoxyl) ethylene diamine are dissolved in an organic solvent, the mixture is heated up to 155-160° C. and hold at that temperature for 4 h or longer time for reflux reaction; after the reaction is completed, unreacted N-(2-ethoxyl) ethylene diamine and organic solvent are separated by rotary evaporation, and thereby a crude product is obtained; wherein, R1 is pentadecyl, heptadecenyl or heptadecyl.

(2) The crude product obtained in the step (1) is heated up to 230-240° C., and is held at the temperature for 4-6 h for further reaction under a reflux condensation condition; thus, a yellow oily liquid is obtained;

(3) The material obtained in the step (2) is treated by reduced pressure distillation in hot state, the product is poured into a mixed solution of ethyl acetate, absolute ethyl alcohol, and petroleum ether mixed in advanced at a volume ratio of 3:3:1 before the product solidifies, the system is agitated vigorously and then kept still so that a solid precipitates; after the system is cooled and crystallized, it is filtered by vacuum filtering, and flushed with the above-mentioned mixed solution; thus, a white semi-solid material is obtained;

(4) The white semi-solid material obtained in the step (3) is dissolved in ether, and then the product is treated by vacuum filtering, washing, and drying; thus, the imidazoline compound described in the present invention is obtained.

In the present invention, the solvent used in the preparation method may be any solvent that can dissolve the above-mentioned raw materials in the art; for example, the solvent may be dimethyl benzene.

In the present invention, the amount of the solvent may be selected conventionally in the art, as long as the raw materials of the reaction can be dissolved in the solvent; preferably, the weight ratio of the organic solvent and N-(2-ethoxyl) ethylene diamine is 8-12:1.

In the preparation method, the amount of $R_1$—COOH and N-(2-ethoxyl) ethylene diamine may be selected according to the ratio of acid and amine in the target product imidazoline compound; preferably, the molar ratio of $R_1$—COOH and N-(2-ethoxyl) ethylene diamine is 0.8-1:1.

In the second aspect, the present invention provides a mobility control system, which comprises the imidazoline compound in the present invention, a mobility control additive, and water.

In the present invention, as an important constituent of the mobility control system, the mobility control additive has an effect of enhancing system mobility control. Preferably, the mobility control additive is selected from the group consisting of sodium salicylate, maleic acid, sodium p-toluene sulfonate, and combinations thereof.

According to a preferred embodiment of the present invention, R is pentadecyl, and the mobility control additive is sodium p-toluenesulfonate. In that preferred embodiment, the mobility control system has a more outstanding mobility control effect.

In the present invention, there is no particular restriction on the contents of the imidazoline compound and the mobility control additive, which is to say, the contents can be selected conventionally in the art; however, to attain a better mobility control effect, preferably, in the mobility control system, the content of the imidazoline compound is 1-10 wt % (e.g., 1 wt %, 2 wt %, 3 wt %, 4 wt %, 5 wt %, 6 wt %, 7 wt %, 8 wt %, 9 wt %, or 10 wt %), the content of the mobility control additive is 0.1-2 wt % (e.g., 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 1.6 wt %, 1.7 wt %, 1.8 wt %, 1.9 wt %, or 2 wt %), and the content of water is 88-98.9 wt %; further preferably, in the mobility control system, the content of the imidazoline compound is 2-6 wt %, the content of the mobility control additive is 0.4-0.8 wt %, and the content of water is 93.2-97.6 wt %.

The mobility control system in the present invention is an intelligent carbon dioxide-sensitive material, which forms a gel material after it contacts with carbon dioxide, and that gel material can attain a plugging effect for gas channeling.

In the third aspect, the present invention provides plugging agent for gas channeling, which is a mixture obtained by introducing carbon dioxide into the mobility control system in the present invention for gel forming.

The viscosity of plugging agent for gas channeling in the present invention can reach as high as $1 \times 10^4$-$20 \times 10^4$ mPa·s, which can fully meet the requirements for plugging for gas channeling.

In the present invention, the volume ratio of the introduced volume of carbon dioxide and the volume of the mobility control system is 1-1.5:1. However, to improve the performance of the mobility control system, preferably, the introducing rate of carbon dioxide is 0.5-1.0 mL/min.

In the third aspect, the present invention provides a method for carbon dioxide flooding, which comprises: injecting the mobility control system in the present invention into an oil reservoir, and then injecting carbon dioxide into the oil reservoir for over-displacement; after the mobility control system forms a plugging agent for gas channeling, further injecting carbon dioxide into the oil reservoir for oil displacement.

In the present invention, the method can achieve carbon dioxide flooding for oil reservoirs within a wide temperature range; preferably, the temperature of the oil reservoir is 40-90° C.

The method for carbon dioxide flooding provided in the present invention can effectively prevent carbon dioxide channeling in the carbon dioxide flooding process for low permeability or ultra-low permeability oil reservoirs; especially, for ultra-low permeability oil reservoirs, the method for carbon dioxide flooding can increase the swept volume of carbon dioxide and improve the oil displacement efficiency, and thereby improve the oil recovery efficiency of ultra-low permeability oil reservoirs.

In the present invention, for ultra-low permeability oil reservoir cores that contain fractures in different widths (wherein, the gas logged permeability of the rock core matrix is about 0.3 mD, the width of fractures is 1-1,000 µm), if the method provided in the present invention is used for carbon dioxide flooding, the plugging efficiency of the plugging agent for gas channeling formed by the mobility control system will be ≥90%.

The plugging efficiency testing method for the mobility control system provided in the present invention when the mobility control system is used for carbon dioxide flooding may be any conventional method in the art; for example, the plugging efficiency testing method may be:

(1) Preparing a rock core that contains fractures: the rock core is assembled from rock core matrix blocks cut along the axial direction manually, with gaps reserved between adjacent rock core matrix blocks, and the width of fractures is controlled by adding stainless steel plates and confining pressure with a core holder;

(2) Oil saturation: crude oil saturation is carried out for the rock core with fractures with vacuum pumping and pressurization devices, and the mass of the rock core with fractures is measured before and after crude oil saturation, so as to obtain the mass of saturated crude oil in the rock core;

(3) Water flooding: water flooding is carried out at 1 mL/min displacement rate with a rock core flooding device, till the water cut reaches 98%;

(4) Carbon dioxide flooding: Carbon dioxide is injected at 1 mL/min injection rate continuously, and the gas injection pressure is monitored; after the pressure is stabilized, the gas injection pressure is logged, and gas logged permeability k1 is calculated;

(5) Injecting mobility control system: the mobility control system in the present invention is injected at 1 mL/min injection rate, and then carbon dioxide is injected for over-displacement;

(6) Gel forming: the rock core is sealed and held at a constant temperature (test temperature) for 10 min., so that a plugging material is formed extensively;

(7) Secondary carbon dioxide flooding: Carbon dioxide is injected at 1 mL/min injection rate continuously again, and the gas injection pressure is monitored; after the pressure is stabilized, the gas injection pressure is logged, and gas logged permeability k2 is calculated;

The permeability is calculated with the following formula:

$$k = \frac{2Q_2 L \mu p_0}{A(p_1^2 - p_2^2)} \times 10^{-1}$$

Where, k is permeability, $\mu m^2$; $Q_2$ is gas flow at the exit side of the rock core, ml/s; L is length of rock core, cm; A is cross-sectional area of rock core, $cm^2$; $P_0$ is absolute atmospheric pressure, MPa; $P_1$ is absolute pressure at the entry side of the rock core, MPa; $P_2$ is absolute pressure at the exit side of the rock core, MPa; and µ is gas viscosity at the test temperature and atmospheric pressure, mPa·s.

The plugging efficiency is calculated with the following formula: plugging efficiency=(k1−k2)/k1.

In the above testing method, the rock core matrix can be commercially available; for example, E-series rock cores (permeability=0.3 mD) from Beijing Shengwei Technology Co. Ltd. may be used; the crude oil is dehydrated and degassed crude oil from a block in Changqing Oil Field.

Hereunder the present invention will be detailed in embodiments. In the following embodiments:

The palmitic acid is from Shanghai Aladdin Biochemical Technology Co., Ltd., with designation as P101059;

The stearic acid is from Shanghai Aladdin Biochemical Technology Co., Ltd., with designation as P108288;

The oleic acid is from Shanghai Aladdin Biochemical Technology Co., Ltd., with designation as O108484;

The N-(2-ethoxyl) ethylene diamine is from Shanghai Aladdin Biochemical Technology Co., Ltd., with designation as H100513;

The infrared spectrometer is from Thermo Nicolet Corporation (a US company), with designation as Nexus;

The NMR spectrometer is from Bruker, with designation as AVANCE III HD 400 Mhz.

Preparation Example 1

Palmitic acid and N-(2-ethoxyl) ethylene diamine (at a molar ratio of 0.83:1) are dissolved in dimethyl benzene (the weight ratio of dimethyl benzene and N-(2-ethoxyl) ethylene diamine is 10:1), the obtained mixture is loaded into a 250 mL three-neck flask equipped with a water separator, and treated by oil-bath heating and refluxing under a magnetic stirring condition, till all of the raw materials are dissolved completely. The target heating temperature is set to 155° C., and the mixture is held at the temperature for 5 h for reflux reaction, till the level of the interface between water and dimethyl benzene in the water separator has no change anymore (i.e., no more water separation); after the reaction is completed, unreacted N-(2-ethoxyl) ethylene diamine and dimethyl benzene solvent are separated and removed by rotary evaporation, and thereby a crude product is obtained; the crude product is heated up to 230° C. in the three-neck flask while it is stirred, and is held at the temperature for 4 h for further reaction under a reflux condensation condition, and finally a yellow oily liquid is obtained; the product is treated by reduced pressure distillation in hot state, the product is poured into a mixed solution of ethyl acetate, absolute ethyl alcohol, and petroleum ether mixed in advanced at a volume ratio of 3:3:1 before the product solidifies, the system is agitated vigorously for 5 min. and then kept still so that a solid precipitates are obtained; after the system is cooled and crystallized, it is filtered by vacuum filtering, and flushed with the above-mentioned mixed solution for 3 times; thus, a white semi-solid material is obtained; the white semi-solid material is dissolved in ether, and then the product is treated by vacuum filtering and washed for 3 times. The product is wrapped in a piece of filter paper, and is loaded into a vacuum drying oven and dried for 24 hr; thus, the target product 1-ethoxyl-2-pentadecyl-imidazoline is obtained.

Figure 2:
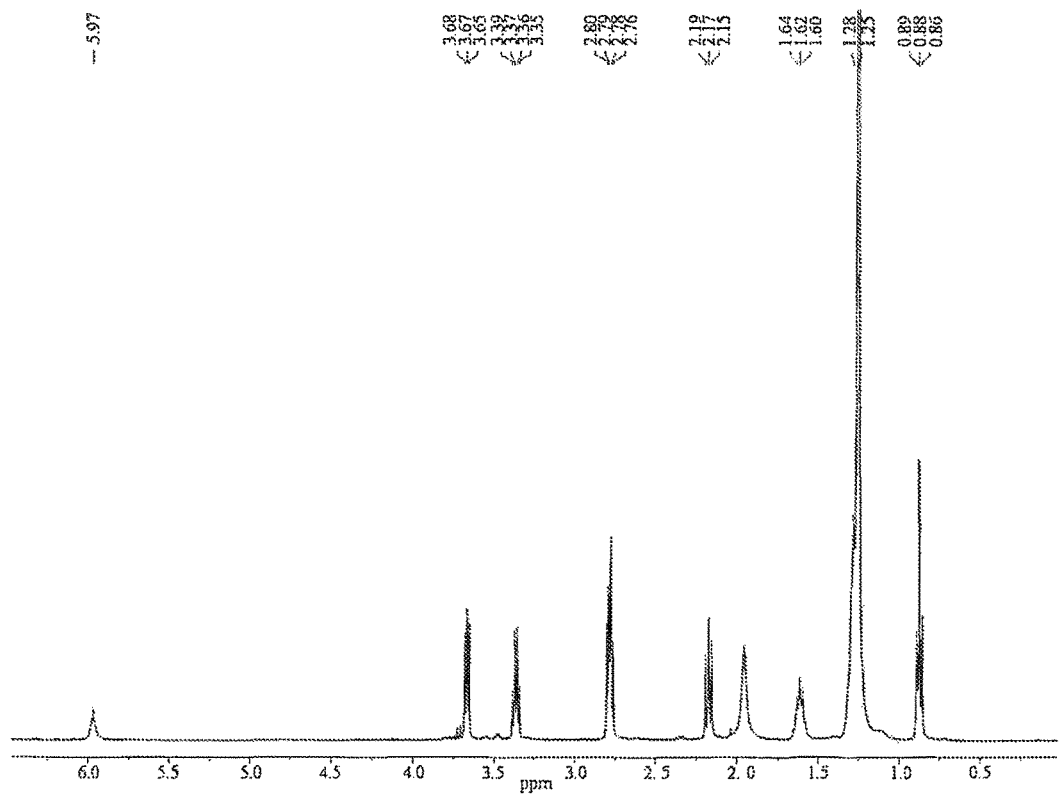
FIG. 2 is a $^1$H-NMR spectrogram of 1-ethoxyl-2-pentadecyl-imidazoline in the preparation example 1.

The target product obtained in the preparation example 1 is measured with an infrared spectrometer and a NMR spectrometer respectively. An infrared spectrogram measured with the infrared spectrometer is shown in FIG. 1, wherein, the peak at 1,056.83 $cm^{-1}$ represents bending vibration of —$(CH_2)_n$— in saturated long-chain alkyl; the peak at 2918.35 $cm^{-1}$ represents symmetric bending vibration of C—H bond in —$CH_3$; the peak at 3299.46 $cm^{-1}$ represents stretching vibration of —OH; the peak at 1640.22 $cm_{-1}$ represents stretching vibration generated by C≡N double bonds in imidazoline;

The H-NMR spectrogram measured with the NMR spectrometer is shown in FIG. 2: 1H NMR (400 MHz, Chloroform-d) δ 5.97 (s, 1H), 3.75-3.57 (m, 2H), 3.37 (q, J=5.7 Hz, 2H), 2.97-2.51 (m, 4H), 2.23-2.11 (m, 2H), 1.68-1.54 (m, 2H), 1.26 (d, J=12.5 Hz, 25H), 0.88 (t, J=6.8 Hz, 3H)

Preparation Example 2

Stearic acid and N-(2-ethoxyl) ethylene diamine (at a molar ratio of 0.9:1) are dissolved in dimethyl benzene (the weight ratio of dimethyl benzene and N-(2-ethoxyl) ethylene diamine is 11:1), the obtained mixture is loaded into a 250 mL three-neck flask equipped with a water separator, and treated by oil-bath heating and refluxing under a magnetic stirring condition, till all of the raw materials are dissolved completely. The target heating temperature is set to 155° C., and the mixture is held at the temperature for 5 h for reflux reaction, till the level of the interface between water and dimethyl benzene in the water separator has no change anymore (i.e., no more water separation); after the reaction is completed, unreacted N-(2-ethoxyl) ethylene diamine and dimethyl benzene solvent are separated and removed by rotary evaporation, and thereby a crude product is obtained; the crude product is heated up to 230° C. in the three-neck flask while it is stirred, and is held at the temperature for 4 hr for further reaction under a reflux condensation condition, and finally a yellow oily liquid is obtained; the product is treated by reduced pressure distillation in hot state, the product is poured into a mixed solution of ethyl acetate, absolute ethyl alcohol, and petroleum ether mixed in advanced at a volume ratio of 3:3:1 before the product solidifies, the system is agitated vigorously for 5 min. and then kept still so that a solid precipitates are obtained; after the system is cooled and crystallized, it is filtered by vacuum filtering, and flushed with the above-mentioned mixed solution for 3 times; thus, a white semi-solid material is obtained; the white semi-solid material is dissolved in ether, and then the product is treated by vacuum filtering and washed for 3 times. The product is wrapped in a piece of filter paper, and is loaded into a vacuum drying oven and dried for 24 hr; thus, the target product 1-ethoxyl-2-heptadecyl-imidazoline is obtained.

Preparation Example 3

Oleic acid and N-(2-ethoxyl) ethylene diamine (at a molar ratio of 1:1) are dissolved in dimethyl benzene (the weight ratio of dimethyl benzene and N-(2-ethoxyl) ethylene diamine is 12:1), the obtained mixture is loaded into a 250 mL three-neck flask equipped with a water separator, and treated by oil-bath heating and refluxing under a magnetic stirring condition, till all of the raw materials are dissolved completely. The target heating temperature is set to 155° C., and the mixture is held at the temperature for 5 hr for reflux reaction, till the level of the interface between water and dimethyl benzene in the water separator has no change anymore (i.e., no more water separation); after the reaction is completed, unreacted N-(2-ethoxyl) ethylene diamine and dimethyl benzene solvent are separated and removed by rotary evaporation, and thereby a crude product is obtained; the crude product is heated up to 230° C. in the three-neck flask while it is stirred, and is held at the temperature for 4 hr for further reaction under a reflux condensation condition, and finally a yellow oily liquid is obtained; the product is treated by reduced pressure distillation in hot state, the product is poured into a mixed solution of ethyl acetate, absolute ethyl alcohol, and petroleum ether mixed in advanced at a volume ratio of 3:3:1 before the product solidifies, the system is agitated vigorously for 5 min. and then kept still so that a solid precipitates are obtained; after the system is cooled and crystallized, it is filtered by vacuum filtering, and flushed with the above-mentioned mixed solution for 3 times; thus, a white semi-solid material is obtained; the white semi-solid material is dissolved in ether, and then the product is treated by vacuum filtering and washed for 3 times. The product is wrapped in a piece of filter paper, and is loaded into a vacuum drying oven and dried for 24 hr; thus, the target product 1-ethoxyl-2-heptadecenyl-imidazoline is obtained.

Example 1

2.0 wt % 1-ethoxyl-2-pentadecyl-imidazoline obtained in the preparation example 1, 0.4 wt % sodium p-toluenesulfonate, and 97.6 wt % water are mixed, to obtain a mobility control system A1.

Example 2

4.0 wt % 1-ethoxyl-2-pentadecyl-imidazoline obtained in the preparation example 1, 0.6 wt % sodium p-toluenesulfonate, and 95.4 wt % water are mixed, to obtain a mobility control system A2.

Example 3

6.0 wt % 1-ethoxyl-2-pentadecyl-imidazoline obtained in the preparation example 1, 0.8 wt % sodium p-toluenesulfonate, and 93.2 wt % water are mixed, to obtain a mobility control system A3.

Example 4

4.0 wt % 2-ethoxyl-2-heptadecyl-imidazoline obtained in the preparation example 2, 0.6 wt % sodium salicylate, and 95.4 wt % water are mixed, to obtain a mobility control system A4.

Example 5

4.0 wt % 1-ethoxyl-2-heptadecenyl-imidazoline obtained in the preparation example 3, 0.6 wt % maleic acid, and 95.4 wt % water are mixed, to obtain a mobility control system A5.

Example 6

2.0 wt % 1-ethoxyl-2-pentadecyl-imidazoline obtained in the preparation example 1, 2.0 wt % 1-ethoxyl-2-heptadecyl-imidazoline obtained in the preparation example 2, 2.0 wt % 1-ethoxyl-2-heptadecenyl-imidazoline obtained in the preparation example 3, 0.8 wt % sodium p-toluenesulfonate, and 93.2 wt % water are mixed, to obtain a mobility control system A6.

Example 7

4.0 wt % 1-ethoxyl-2-pentadecy-imidazoline obtained in the preparation example 1, 0.2 wt % sodium p-toluenesulfonate, 0.2 wt % sodium salicylate, 0.2 wt % maleic acid, and 95.4 wt % water are mixed, to obtain a mobility control system A7.

Example 8

10.0 wt % 1-ethoxyl-2-pentadecyl-imidazoline obtained in the preparation example 1, 0.1 wt % sodium p-toluenesulfonate, and 89.9 wt % water are mixed, to obtain a mobility control system A8.

Example 9

1.0 wt % 1-ethoxyl-2-pentadecyl-imidazoline obtained in the preparation example 1, 2.0 wt % sodium p-toluenesulfonate, and 97.0 wt % water are mixed, to obtain a mobility control system A9.

Example 10

4.0 wt % 1-ethoxyl-2-pentadecyl-imidazoline obtained in the preparation example 1, 0.6 wt % sodium salicylate, and 95.4 wt % water are mixed, to obtain a mobility control system A10.

Measurements (1) Viscosity of the mobility control system: The viscosity values of A1-A10 sheared at 25° C. and 7.34 s$^{-1}$ shearing rate for 10 min are measured respectively with a rheometer (from Thermo Fisher SCIENTIFIC, with designation as Haake MARS 60, the same below). The result is shown in Table 1.

(2) Viscosity of the plugging agent for gas channeling formed by the mobility control system: Carbon dioxide is introduced (at 1.0 ml/min introducing rate, the volume ratio of the introduced volume of carbon dioxide and the volume of the mobility control system is 1:1) into the mobility control systems A1-A10 at different temperatures (40° C., 65° C., and 90° C.) respectively, to form plugging agents for gas channeling. The viscosity values of the plugging agents for gas channeling sheared at corresponding temperatures and 7.34 s$^{-1}$ shearing rate for 10 min are measured respectively with a rheometer. The result is shown in Table 2.

(3) Plugging efficiency under different fracture and temperature conditions: the plugging efficiency of each of the mobility control systems A1-A10 in factures in different widths (50 μm, 300 μm, and 900 μm) at different temperatures (40° C., 65° C., and 90° C.) is tested respectively with the plugging efficiency testing method described in the present invention. The result is shown in Table 3.

TABLE 1

| | A1 | A2 | A3 | A4 | A5 | A6 | A7 | A8 | A9 | A10 |
|---|---|---|---|---|---|---|---|---|---|---|
| Viscosity, mPa · s | 5 | 5 | 6 | 7 | 8 | 10 | 7 | 6 | 5 | 7 |

It can be seen from the result in Table 1: the mobility control system in the present invention has initial viscosity as low as 5-10 mPa·s, and has favorable injection performance. It can penetrate into the deep channel easily, so that the deep channels are plugged off.

TABLE 2

| | Viscosity of Plugging Agent for Gas Channeling Formed at Different Temperatures, mPa · s | | |
|---|---|---|---|
| | 40° C. | 65° C. | 90° C. |
| A1 | 5.0 × 10$^4$ | 4.2 × 10$^4$ | 2.6 × 10$^4$ |
| A2 | 7.0 × 10$^4$ | 6.0 × 10$^4$ | 4.5 × 10$^4$ |
| A3 | 12.0 × 10$^4$ | 10.0 × 10$^4$ | 7.0 × 10$^4$ |
| A4 | 5.8 × 10$^4$ | 4.4 × 10$^4$ | 3.0 × 10$^4$ |
| A5 | 6.2 × 10$^4$ | 5.1 × 10$^4$ | 3.1 × 10$^4$ |
| A6 | 10.1 × 10$^4$ | 8.6 × 10$^4$ | 6.0 × 10$^4$ |
| A7 | 6.3 × 10$^4$ | 5.3 × 10$^4$ | 3.2 × 10$^4$ |
| A8 | 4.5 × 10$^4$ | 3.8 × 10$^4$ | 2.2 × 10$^4$ |
| A9 | 2.6 × 10$^4$ | 2.0 × 10$^4$ | 1.2 × 10$^4$ |
| A10 | 5.2 × 10$^4$ | 4.3 × 10$^4$ | 2.7 × 10$^4$ |

Figure 3:
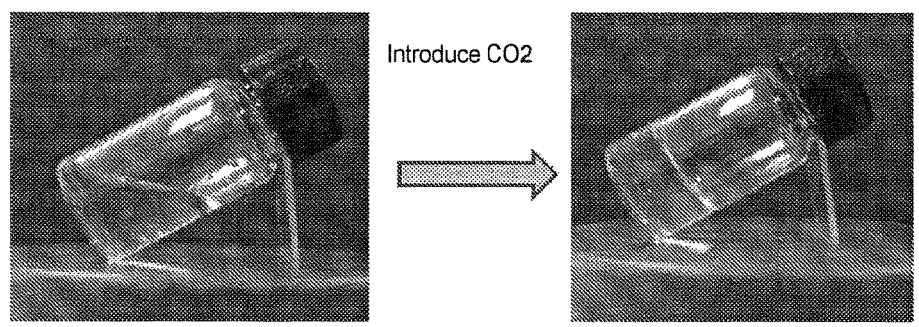
FIG. 3 is a viscosity comparison diagram before/after the mobility control system in example 2 interacts with carbon dioxide at 40° C.

It can be seen from the result in Table 2: the mobility control system in the present invention interacts with carbon dioxide and form a plugging agent for gas channeling that has viscosity as high as 1×10$^4$-20×10$^4$ mPa·s at 40-90° C., which is favorable for deep plugging in carbon dioxide flooding oil reservoirs, and can increase the swept volume of carbon dioxide flooding. Moreover, it can be seen intuitively from FIG. 3: the viscosity of the plugging agent for gas channeling formed by the mobility control system in the present invention and carbon dioxide is remarkably increased, which indicates that the mobility control system in the present invention has highly carbon dioxide sensitivity.

TABLE 3

| | Plugging Efficiency under Different Fracture and Temperature Conditions, % | | | | | | | | |
|---|---|---|---|---|---|---|---|---|---|
| | Temperature | | | | | | | | |
| | 40° C. | | | 65° C. | | | 90° C. | | |
| | Width of fracture | | | | | | | | |
| | 50 μm | 300 μm | 900 μm | 50 μm | 300 μm | 900 μm | 50 μm | 300 μm | 900 μm |
| A1 | 96.3 | 93.5 | 90.6 | 94.8 | 91.5 | 87.6 | 93.3 | 88.5 | 81.6 |
| A2 | 98.6 | 94.8 | 91.3 | 97.1 | 92.8 | 88.3 | 95.6 | 89.8 | 82.3 |
| A3 | 99.4 | 96.4 | 91.9 | 97.9 | 94.4 | 88.9 | 96.4 | 91.4 | 82.9 |
| A4 | 96.9 | 94.0 | 90.7 | 95.4 | 92.0 | 87.7 | 93.9 | 89.0 | 81.7 |
| A5 | 97.0 | 94.2 | 90.9 | 95.5 | 92.2 | 87.9 | 94.0 | 89.2 | 81.9 |
| A6 | 99.0 | 95.8 | 91.6 | 97.5 | 93.8 | 88.6 | 96.0 | 90.8 | 82.6 |
| A7 | 97.4 | 94.6 | 91.1 | 95.9 | 92.6 | 88.1 | 94.4 | 89.6 | 82.1 |
| A8 | 96.1 | 92.6 | 90.3 | 94.6 | 90.6 | 87.3 | 93.1 | 87.6 | 81.3 |
| A9 | 94.1 | 92.3 | 90.0 | 92.6 | 90.3 | 87.0 | 91.1 | 87.3 | 81.0 |
| A10 | 96.6 | 93.8 | 90.5 | 95.1 | 91.8 | 87.5 | 93.6 | 88.8 | 81.5 |

It can be seen from the result in Table 3: the mobility control system in the present invention interacts with carbon dioxide in cores and thereby forms a plugging agent for gas channeling that has outstanding plugging performance.

While the present invention is described above in detail in some preferred embodiments, the present invention is not limited to those embodiments. Various simple variations, including combinations of the technical features in any other appropriate way, can be made to the technical scheme of the present invention within the scope of the technical concept of the present invention, but such variations and combinations shall be deemed as disclosed content in the present invention and falling in the protection scope of the present invention.

We claim:

1. A mobility control system comprising the imidazoline compound represented by formula (1), a mobility control additive, and water;

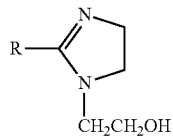

formula (1)

wherein R is pentadecyl, and the mobility control additive is sodium p-toluene sulfonate.

2. The mobility control system of claim 1, wherein, as percentages of the weight of the mobility control system, the content of the imidazoline compound is 1-10 wt. %, the content of the mobility control additive is 0.1-2 wt. %, and the content of water is 88-98.9 wt. %.

3. The mobility control system of claim 2, wherein, as percentages of the weight of the mobility control system, the content of the imidazoline compound is 2-6 wt. %, the content of the mobility control additive is 0.4-0.8 wt. %, and the content of water is 93.2-97.6 wt. %.

4. A plugging agent for gas channeling, wherein the plugging agent for gas channeling is a mixture obtained by introducing carbon dioxide into the mobility control system of claim 1 to form a gel.

5. The plugging agent for gas channeling of claim 4, wherein, as percentages of the weight of the mobility control system, the content of the imidazoline compound is 1-10 wt. %, the content of the mobility control additive is 0.1-2 wt. %, and the content of water is 88-98.9 wt. %.

6. The plugging agent for gas channeling of claim 4, wherein, as percentages of the weight of the mobility control system, the content of the imidazoline compound is 2-6 wt. %, the content of the mobility control additive is 0.4-0.8 wt. %, and the content of water is 93.2-97.6 wt. %.

* * * * *